United States Patent [19]
Patel et al.

[11] Patent Number: 4,853,027
[45] Date of Patent: Aug. 1, 1989

[54] PHYTOTOXIC 2-ALKYL-5-(HETEROCYCLIC)-PYRROLE-3,4-DICARBOXYLATES

[75] Inventors: Kanu M. Patel, Wilmington; James E. Powell, Greenville, both of Del.

[73] Assignee: E. I. Du Pont de Nemours and Company, Wilmington, Del.

[21] Appl. No.: 3,233

[22] Filed: Jan. 14, 1987

Related U.S. Application Data

[63] Continuation-in-part of Ser. No. 904,323, Sep. 8, 1986, abandoned.

[51] Int. Cl.$^4$ .................... C07D 401/04; A01N 43/40
[52] U.S. Cl. ........................ 71/94; 546/281; 544/333; 544/405; 548/128; 548/131; 548/242; 548/336; 548/374
[58] Field of Search ............................ 546/281; 71/94

[56] References Cited

U.S. PATENT DOCUMENTS 4,643,995  2/1987  Engel et al. .................... 514/210

Primary Examiner—Alan L. Rotman

[57] ABSTRACT

Phytotoxic 2-methyl-5-(heterocyclic)-pyrrole-3,4-dicarboxylates.

13 Claims, No Drawings

PHYTOTOXIC 2-ALKYL-5-(HETEROCYCLIC)-PYRROLE-3,4-DICARBOXYLATES

RELATED APPLICATION

This application is a continuation-in-part of application Ser. No. 904,323, filed on Sept. 8, 1986, now abandoned.

DESCRIPTION OF THE INVENTION

It has been found that useful phytotoxic properties are possessed by compounds of the formula:

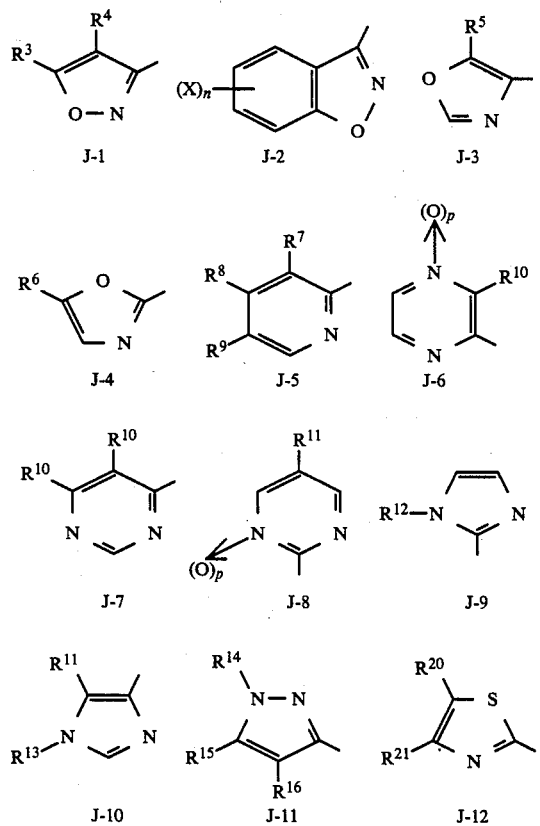

wherein

R and $R^1$ each independently is alkyl, mono- or polyhaloalkyl, alkenyl or alkynyl of up to four carbon atoms, and A is $C_1$ to $C_3$ alkyl;

J is one of the moieties

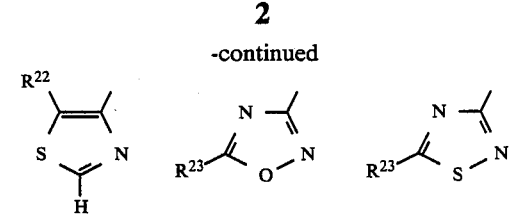

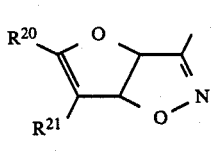

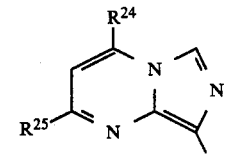

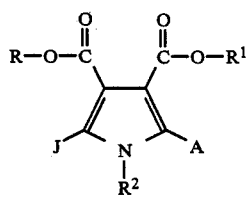

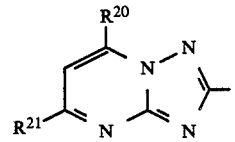

wherein n=zero, one or two and each X independently is halogen or nitro, or alkyl or alkoxy of one to four carbon atoms, and $R^2$ is (a) hydrogen;

(b) hydroxymethyl;

(c) —B(alkyl)$_2$ of two to six carbon atoms, where B is the symbol for Boron, (d) —C(O)$R^{17}$ of one to eight carbon atoms; wherein $R^{17}$ is hydrogen, alkyl, alkenyl, alkynyl, cycloalkyl, cycloalkylalkyl, alkoxy, aryl, aryloxy, heteroaryl, arylalkyl, heteroarylalkyl or such substituted by one to a plurality of halogen atoms and/or by one of alkoxy, alkylthio, alkyl, alkoxycarbonyl, carboxyl, alkylsulfinyl and alkylsulfonyl;

(e) —CH$_2$—O—C(O)—$R^{18}$ wherein $R^{18}$ is a moiety defined by $R^{17}$;

(f) —S—C(O)O—$R^{19}$, wherein $R^{19}$ is alkyl or phenyl.

$R^3$, $R^4$ and $R^6$ each independently is hydrogen, or has one to six carbon atoms and is one of alkyl, monohaloalkyl, polyhaloalkyl, alkoxyalkyl, alkylthioalkyl, or has six to ten carbon atoms and is phenyl or phenylalkyl or either substituted by from one to three halogen atoms and/or by one of alkyl, alkoxy and alkylthio, with the proviso that $R^3$ and $R^4$ together can represent the valence bonds of an alkylene moiety —(CH$_2$)$_m$—, wherein m is three, four or five ;

$R^5$ has one to six carbon atoms, and is alkyl, mono- or polyhaloalkyl, alkoxyalkyl, alkylthioalkyl, alkylsulfinylalkyl, alkylsulfonylalkyl, alkoxycarbonylalkyl, dialkoxyphosphinylalkyl, or has six to ten carbon atoms and is phenyl, phenylalkyl, phenoxyalkyl, phenylthioalkyl, phenylsulfinylalkyl or phenylsulfonylalkyl;

$R^7$, $R^8$ and $R^9$ each independently is hydrogen, halogen, trifluoroethoxy, difluoromethoxy, cyano, nitro, hydroxy, amino, alkyl, alkoxy, mono- or dialkoxyalkyl, alkylthio, mono- or dialkylamino, wherein each alkyl moiety is of one to four carbon atoms;

each of $R^{10}$ independently is hydrogen; halogen; cyano; or alkyl or alkoxy of one to four carbon atoms;

each of $R^{11}$ independently is hydrogen; alkyl of one to four carbon atoms; or phenyl optionally substituted by one or more halogen atoms and/or one or two of alkyl, mono- and poly-haloalkyl and alkoxy of one to four carbon atoms;

$R^{12}$ is alkyl of one to four carbon atoms; phenyl, or phenylalkyl of seven to ten carbon atoms or either substituted by one or more halogen atoms, and/or one or two of alkyl, mono- and poly-haloalkyl and alkoxy of one to four carbon atoms;

$R^{13}$, $R^{14}$, $R^{15}$ and $R^{16}$ independently are alkyl of one to four carbon atoms; or phenyl optionally substituted by one or more halogen atoms, and/or one or two of alkyl, mono- and polyhaloalkyl and alkoxy of one to four carbon atoms, with the proviso that $R^{15}$ and $R^{16}$ together can represent the valence bonds of an alkylene moiety $(CH_2)_m$ where $m=3$, 4 or 5;

p is zero or one;

$R^{20}$ and $R^{21}$ are independently H or alkyl;

$R^{22}$ is H, alkylthio, alkylsulfinyl or alkylsulfonyl;

$R^{23}$ is alkyl or phenyl optionally substituted by F, Cl, $CH_3$ or $OCH_3$;

$R^{24}$ and $R^{25}$ are independently H, alkyl or halide.

Preferred for reasons of increased ease of synthesis and/or greater herbicidal efficacy are:

1. Compounds of Formula I where
A is $CH_3$;
R is $C_1$ to $C_3$ alkyl, $C_2$ to $C_3$ haloalkyl, allyl or propargyl;
$R^1$ is $C_1$ to $C_2$ alkyl;
$R^2$ is hydrogen, hydroxymethyl, $C(O)R^{17}$ or $CH_2OC(O)R^{18}$; and
$R^{17}$ and $R^{18}$ are independently $C_1$ to $C_4$ alkyl, $C_5$ to $C_6$ cycloalkyl, phenyl, or pyridinyl or such substituted by one or more of halogen atoms and/or one of alkoxy, alkylthio, alkyl, alkoxycarbonyl, carboxyl, alkylsulfinyl or alkylsulfonyl.

2. Compounds of Preferred 1 where
$R^3$, $R^4$ and $R^6$ each independently is hydrogen, $C_1$ to $C_4$ alkyl, mono- or polyhaloalkyl, alkoxyalkyl, or alkylthioalkyl, or is phenyl or benzyl;
$R^5$ is $C_1$ to $C_4$ alkyl, alkoxyalkyl, alkylthioalkyl, alkylsulfinylalkyl, alkylsulfonylalkyl, phenyl or benzyl;
$R^7$, $R^8$ and $R^9$ each independently is hydrogen, chlorine, or is $C_1$ to $C_4$ alkyl, alkoxy or alkylthio;
each of $R^{10}$ independently is hydrogen, chlorine, or is $C_1$ to $C_4$ alkyl or alkoxy;
each of $R^{11}$ independently is hydrogen, $C_1$ to $C_4$ alkyl, or phenyl optionally substituted by one or more chlorine atoms and/or one or two methyl, methoxy or trifluoromethyl groups;
$R^{12}$ is $C_1$ to $C_4$ alkyl, or is phenyl or benzyl optionally substituted by one or two chlorine atoms and/or one or two methyl, methoxyl, or trifluoromethyl groups;
$R^{13}$, $R^{14}$, $R^{15}$ and $R^{16}$ each independently is $C_1$ to $C_4$ alkyl, or is phenyl optionally substituted by one or more chlorine atoms and/or one or two methyl, methoxy or trifluoromethyl groups; or $R^{15}$ and $R^{16}$ together represent $(CH_2)_m$-where m is 3 or 4.

3. Compounds of Preferred 2 where J is J-1.
4. Compounds of Preferred 2 where J is J-2.
5. Compounds of Preferred 2 where J is J-3.
6. Compounds of Preferred 2 where J is J-4.
7. Compounds of Preferred 2 where J is J-5.
8. Compounds of Preferred 2 where J is J-6.
9. Compounds of Preferred 2 where J is J-7.
10. Compounds of Preferred 2 where J is J-8.
11. Compounds of Preferred 2 where J is J-9.
12. Compounds of Preferred 2 where J is J-10.
13. Compounds of Preferred 2 where J is J-11.
14. Compounds of Preferred 2 where J is J-12.
15. Compounds of Preferred 2 where J is J-13.
16. Compounds of Preferred 2 where J is J-14.
17. Compounds of Preferred 2 where J is J-15.
18. Compounds of Preferred 2 where J is J-16.
19. Compounds of Preferred 2 where J is J-17.
20. Compounds of Preferred 2 where J is J-18.
21. Compounds of Formula I where J is J-1, J-3, J-5, J-6, J-8 or J-11.

A preferred subgenus of the compounds of Formula I is composed of those individual species wherein A is $CH_3$, J is J-1, J-2, J-3 or J-4 wherein R and $R^1$ each is alkyl—particularly methyl—n is zero, and each of $R^3$, $R^4$, $R^5$ and $R^6$ is hydrogen or alkyl—particularly methyl, and particularly those wherein J is J-3, $R^2$ is hydrogen, and $R^5$ is methyl.

Another preferred subgenus of the compounds of Formula I is composed of those individual species wherein J is J-5 wherein R and $R^1$ each is alkyl—particularly methyl—$R^7$, $R^8$ and $R^9$ each is hydrogen, halogen, alkyl, alkoxy, alkylthio, difluoromethoxy, or mono- or dialkoxymethyl, and $R^2$ is hydrogen.

Yet another preferred subgenus of the compounds of Formula I is composed of those individual species wherein J is J-6, p is zero, R and $R^1$ each is alkyl—particularly methyl—and $R^{10}$ is hydrogen, alkyl—particularly methyl—or halogen—particularly chlorine.

The preparation, isolation and testing of typical individual species of the compounds of Formula I are described in the examples, following. The genus of compounds is further illustrated and exemplified by the following further individual species, all of which are specifically contemplated in this invention. In the interest of brevity, and clarity, and to avoid repetition of sometimes long chemical names, these species will be identified in terms of Formula I and the symbols used therein. In all cases, the moieties R and $R^1$ each is methyl, and $R^2$ is hydrogen.

First subclass, J is J-3, the moiety $R^5$ in each case being as follows:

| Species | $R^5$ |
|---------|-------|
| A | ethyl |
| B | methoxymethyl |
| C | methylthiomethyl |
| D | methylsulfinylmethyl |
| E | methylsulfonylmethyl |
| F | 2,4-dichlorophenoxymethyl |
| G | methoxycarbonylmethyl |
| H | benzyl |
| I | trifluoromethyl |

Second subclass, J is J-5, $R^7$, $R^8$ and $R^9$ being the following:

| Species | $R^7$ | $R^8$ | $R^9$ |
|---------|-------|-------|-------|
| J | methyl | methyl | hydrogen |
| K | ethyl | hydrogen | hydrogen |
| L | hydroxy | hydrogen | hydrogen |
| M | isopropoxy | hydrogen | hydrogen |
| N | hydroxymethyl | hydrogen | hydrogen |
| O | cyano | hydrogen | hydrogen |
| P | hydrogen | cyano | hydrogen |
| Q | dimethylamino | hydrogen | hydrogen |
| R | methyl | cyano | hydrogen |
| S | trifluoromethyl | hydrogen | chlorine |
| T | chlorine | hydrogen | methoxy |
| U | methyl | nitro | hydrogen |
| V | methyl | hydrogen | methyl |

Further illustrative examples of the compounds of Formula I wherein J is J-5 and $R^2$ is other than hydrogen are as follows, in all cases R and $R^1$ each being methyl, and $R^7$, $R^8$ and $R^9$ each being hydrogen:

| Species | $R^2$ |
|---|---|
| W | acetyl |
| X | acetoxymethyl |
| Y | cyclopropylcarbonyloxymethyl |
| Z | phenylcarbonyloxymethyl |
| AA | 1,1-dimethylethylcarbonyloxymethyl |
| AB | 2-carboxyethylcarbonyloxymethyl |
| AC | 2-carboxy-4-cyclohexen-1-ylcarbonyloxymethyl |
| AD | 2-pyridinylcarbonyloxymethyl |
| AE | methylthiomethylcarbonyloxymethyl |
| AF | methylsulfinylmethylcarbonyloxymethyl |
| AG | methylsulfonylmethylcarbonyloxymethyl |
| AH | 3-pyridinylcarbonyloxymethyl |
| AI | hydroxymethyl |
| AJ | cyclopropylcarbonyl |
| AK | (1-methylpropyl)oxycarbonylthio |

| Third subclass, J is J-6, p is zero, | |
|---|---|
| Species | $R^{10}$ |
| AL | cyano |
| AM | bromo |

| Fourth subclass, J is J-7, | |
|---|---|
| Species | $R^{10}$ |
| AN | 5-bromo |
| AO | 5-(methoxy) |
| AP | 5-chloro-6-methyl |

| Fifth subclass, J is J-8, p is zero, | |
|---|---|
| Species | $R^{11}$ |
| AQ | methyl |
| AR | phenyl |

| Sixth subclass, J is J-9, | |
|---|---|
| Species | $R^{12}$ |
| AS | ethyl |

| Seventh subclass, J is J-10, | | |
|---|---|---|
| Species | $R^{11}$ | $R^{13}$ |
| AT | hydrogen | ethyl |
| AU | methyl | methyl |
| AV | methyl | ethyl |

| Eighth subclass, J is J-11, | | | |
|---|---|---|---|
| Species | $R^{14}$ | $R^{15}$ | $R^{16}$ |
| AW | methyl | ethyl | hydrogen |
| AX | ethyl | pheny | hydrogen |
| AY | methyl | methyl | methyl |

Some compounds of Formula I can be prepared by treating an N-(J-carbonyl)alanine (A is $CH_3$, or analogously where A is $C_2$ to $C_3$ alkyl)

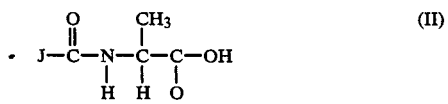

with an R, $R^1$-diester of acetylenedicarboxylic acid

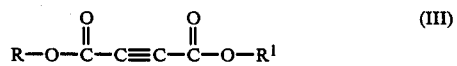

in the presence of acetic anhydride. The reaction is effected by heating the reagents together at a temperature of about 60°–65° C.

The acid II can be prepared by conventional means from a corresponding alkyl ester:

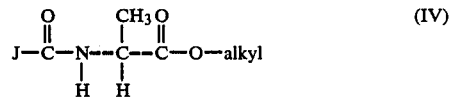

which in turn can be prepared by treating a J-carboxylic acid with 1,1'-carbonyldiimidazole (CDI), then treating the mixture with an appropriate alkyl ester of alanine, according to the equation

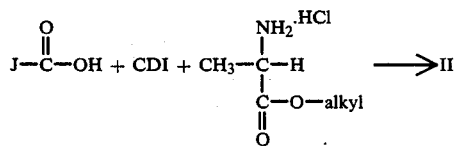

The treatment suitably is conducted by stirring the reagents in a solvent such as tetrahydrofuran (THF) at or somewhat above room temperature.

Compounds of Formula I can also be prepared by treating a diketone of the formula

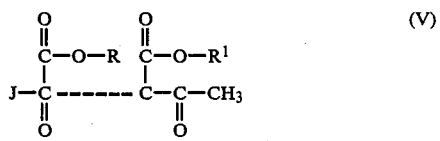

with ammonium acetate. The cyclization is effected by (a) heating a mixture of the diketone, ammonium acetate and a substantial amount of acetic acid, as solvent, or (b) by heating a mixture of the diketone, ammonium acetate, a lower alkanol as solvent and a catalytic amount of acetic acid.

Diketones of Formula V can be prepared by treating an R-ester of the 3-J-3 oxopropanoic acid, this beta-ketoester having the formula

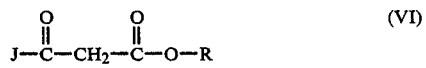

with an $R^1$-ester of acetoacetic acid of the formula

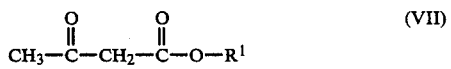

under basic conditions in the presence of iodine. Treatment of the ketoester VI with the ester VII is carried out by treating the ester VI with a base such as sodium hydride in a solvent such as ether, treating the ester VII similarly, then slowly mixing the resulting solutions and heating the mixture. The resulting mixture is treated with a solution of iodine in ether, and that mixture is warmed to complete the reaction.

Alternatively, the ketoester VI is converted to a carbanion, which is treated with an $R^1$ ester of 2-chloroacetoacetic acid of the formula

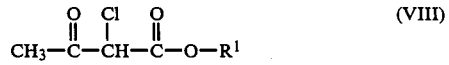

to give a diketone of Formula V. The carbanion is formed by treating the ketoester VI with an alkali metal alkoxide, supported upon neutral alumina, to form the carbanion of the formula

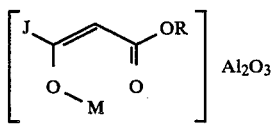

(IX)

Preparation of the alkoxide/alumina reagent and treatment of the ketoester VI with that reagent follow methodology described by G. Bram, et al., Synthetic Communications, 1980, Volume 10, pages 279–289, and J. A. M. van den Goorbergh and A. van der Gen, Recueil Trav. Chim. Pays-Bas, 1984, volume 103, pages 90–96: the alkoxide/alumina reagent is prepared by stirring together a solution of the alkoxide in equal parts of the corresponding alcohol and tetrahydrofuran (THF) and a powdered activated neutral alumina, and removing the solvents. Stirring together a solution of the ketoester VI in THF and the alkoxide/alumina reagent forms the carbanion.

The carbanion IX then is treated with the ester of 2-chloroacetoacetic acid VIII by mixing the two at about room temperature to give the diketone V.

Beta-ketoesters of Formula VI can be prepared by three variations of the Claisen Condensation, to wit:

(1) treating a hot stirred mixture of an alkali metal alkoxide and benzene with a mixture of an alkyl-ester of a J acid, J-C(O)O-(lower alkyl), and an R-ester of acetic acid;

(2) adding a methyl J ketone,

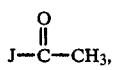

to a hot mixture of a di-R carbonate, sodium hydride and benzene;

(3) heating a mixture of an alkyl ester of J acid (defined in 1, above), an R ester of acetic acid and a base, such as sodium hydride.

Some compounds of Formula I also can be prepared according to the following sequence of reactions:

(1) a beta-ketoester VI is treated with an $R^1$ ester of 2-chloro-3-(tosylhydrazono)butanoic acid of the formula (shown for A is $CH_3$, or analogously for A is $C_2$ to $C_3$ alkyl)

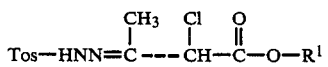

(X)

in the presence of an alkali metal alkoxide, to form an $R,R^1$-diester of 2-(1-(tosylhydrazono)ethyl)-3-(J-carbonyl)-1,4-butanedioic acid,

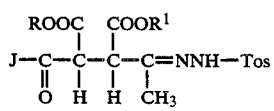

(XI)

The treatment can be conducted by treating a solution of the ketoester VI in a solvent such as THF with a solution of the alkoxide in the corresponding alcohol, then adding a solution of the ester X in the same solvent.

(2) A solution of the diester XI in methanol is treated with hydrogen chloride as to form the $R,R^1$-diester of 2-methyl-1-(tosylamino)-5-(J)pyrrole-3,4-dicarboxylic acid, (shown for A is $CH_3$ or analogously for A is $C_2$ to $C_3$ alkyl)

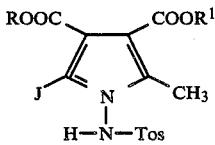

(XII)

which is then dissolved in methanol and hydrogenolyzed in the presence of Raney nickel to give the compound of Formula I.

The ester X can be prepared by treating a solution of tosylhydrazine in a solvent such as THF with a solution of the $R^1$-ester of 2-chloroacetoacetic acid in the same solvent according to the procedure of T. L. Gilchrist, et al., Journal of the Chemical Society, Perkin Transactions I, pages 1803–7 (1983).

N-derivatives ($R^2$ is other than hydrogen) can be prepared from the $R^2$=hydrogen precursor by conventional techniques.

The following examples describe the preparation, isolation and physical properties of typical individual species of the compounds of Formula I, in particular instances. In each case, the identity of each product, and each of any intermediate involved, was confirmed by appropriate chemical and spectral analyses.

EXAMPLE 1

Dimethyl 2-methyl-5-(5-methyl-3-isoxazolyl)pyrrole-3,4-dicarboxylate (1)

A mixture of 1.55 g of ethyl 5-methyl-3-isoxazolecarboxylate (1A) (P. G. Baraldi, et al., Journal of Heterocyclic Chemistry, volume 19, pages 557–560 (1982)) and 20 ml of 10% w:v sodium hydroxide in water was stirred at room temperature for 2 hours. The resulting mixture was cooled to 0° C., acidified with 6N hydrochloric acid to pH 3, saturated with sodium chloride and extracted with ethyl acetate. The extract was dried (MgSO$_4$) and stripped of solvent to give 5-methyl-3-isoxazolecarboxylic acid (1B), as a solid, m.p.: 170°–172° C. (with decomposition).

8.2 g of 1,1'-carbonyldiimidazole (CDI) was added to a mixture of 6.35 g of 1B and 75 ml of dry tetrahydrofuran (THF) and the mixture was stirred for 2 hours at room temperature. Then 7.5 g of alanine ethyl ester hydrochloride was added, the mixture was stirred overnight, filtered, and the filtrate was stripped of solvent. The residue was dissolved in 100 ml of a 9:1 v:v mixture of methylene chloride and ethyl acetate, the solution was filtered through silica gel, the gel was washed with 900 ml of the same solvent, then the combined filtrate and washings was stripped of solvent. The residue was a yellow oil that crystallized on standing. The crystals were washed with pentane and dried, to give N-(5-methyl-3-isoxazolylcarbonyl)alanine ethyl ester (1C), as a solid, m.p.: 65°–66° C. 1C was converted to the corresponding acid (1D, a solid, m.p.: 148°–150° C.) in the manner that 1A was converted to 1B.

1.98 g of 1D was added to a mixture of 15 ml of acetic anhydride and 2.8 g of dimethyl acetylenedicarboxylate (DMADC), and the mixture was heated at 130° C. for 1 hour. Then the solution was concentrated under vacuum and the residue was chromatographed on silica gel, with a 9:1 v:v mixture of methylene chloride and ethyl acetate as eluent, to give a fraction which was stripped of solvent to give 1, as a crystalline solid, m.p.: 161°–162° C. (with decomposition).

EXAMPLE 2

Dimethyl 2-methyl-5-(4-methyl-3-isoxazolyl)pyrrole-3,4-dicarboxylate (2)

A mixture of 116 g of propionaldehyde, 1020 g of acetic anhydride and 404.8 g of triethylamine was stirred at room temperature while 24.4 g of 4-dimethylaminopyridine (DMAP) was added, causing the mixture to warm to 34° C. The mixture was stirred at room temperature over a weekend, poured onto 1.24 kg of ice and the resulting mixture was stirred with cooling (dry ice/acetone, −40° to −20° C.) for 1 hour. The aqueous phase was separated and extracted with 2 liters of ether. The extract was washed with saturated aqueous sodium bicarbonate solution until neutral, then with water, and brine, and dried (MgSO$_4$). 1.8 liters of ether were evaporated, and the residue was distilled in a Vigreaux column to give B 1-propenyl acetate (2A), b.p.: 92°–105° C./1 Torr.

A solution of 12.8 g of ethyl chloro(hydroxyimino)acetate in 45 ml of absolute ether was added dropwise over 30 minutes to a refluxing solution of 82.4 g of 2A and 8.3 g of triethylamine in 120 ml of ether, and the mixture was heated at reflux for 3 hours. The mixture was cooled and poured into 400 ml of water, the ether layer was separated, dried (MgSO$_4$) and stripped of solvent. The residue was heated for 2 hours at 180° C., then a short-path stillhead was fitted to the flask and acetic acid was distilled off (110°–115° C.) over 90 minutes. The residue was chromatographed on silica gel with a 3:2 v:v mixture of methylene chloride and hexane as eluent. The middle fraction of three afforded ethyl 4-methylisoxazole-3-carboxylate (2B), a light yellow solid, m.p.: 50.5°–52.5° C.

A solution of 2.8 g of 2B in 5.4 ml of methyl acetate was added to 1 g of sodium hyride, and the mixture was heated at reflux for 7 hours, then 0.25 ml of methanol was added. When gas evolution ended, the mixture was heated at reflux for 15 minutes, then cooled and stirred at room temperature overnight. The mixture was quenched in water, the resulting mixture was acidified with glacial acetic acid, and extracted with methylene chloride. The extract was dried (MgSO$_4$) and stripped of solvent. The residue was chromatographed on silica gel with a 1:3 v:v mixture of ethyl acetate and hexane as eluent. The middle fractions that were obtained gave ethyl 3-(4-methyl-3-isoxazolyl)-3-oxopropionate (2C), as a light yellow oil. 27 g of sodium methoxide was dissolved in a mixture of 100 ml of methanol and 100 ml of THF. 50 grams of aluminum oxide (activated, neutral, Brockmann I, Aldrich) was added and the mixture was stirred for 30 minutes. The solvents were removed under reduced pressure to give aluminum oxide-supported sodium-methoxide (2D).

1.2 g of 2D was added to a solution of 1.9 g of 2C in 10 ml of anhydrous THF and the mixture was stirred at room temperature for 1 hour. Then the mixture was stripped of solvent, 2.7 ml of methyl 2-chloroacetoacetate was added and the mixture was stirred at room temperature for 5 days. The mixture was slurried in methylene chloride and filtered. The filtrate was stripped of solvent, then distilled in a Kugelrohr apparatus (80° C./0.05 Torr.). The residue was mixed with 1.5 g of ammonium acetate, 20 ml of methanol and 4 drops of glacial acetic acid and the mixture was heated at reflux for 3 hours. The mixture was cooled to room temperature, stripped of volatiles, mixed with 70 ml of water, and extracted with methylene chloride. The extract was washed with saturated aqueous sodium chloride solution, dried (Na$_2$SO$_4$) and stripped of solvent. The residue was chromatographed on silica gel with a 1:1 v:v ethyl acetate/hexane mixture as eluent. The middle fractions gave 2, as a yellow solid, m.p.: 130°–134° C.

EXAMPLE 3

Dimethyl 5-methyl-2-(3-benzisoxazolyl)pyrrole-3,4-dicarboxylate (3)

A mixture of 50 g of ethyl (2-nitrophenyl)acetate, 30 g of isoamyl nitrite and 400 ml of ethanol was added to sodium ethoxide prepared by treating 5.1 g of sodium with 100 ml of ethanol and diluting with ethanol to 100 ml. The mixture was heated at 50°–60° C. for 4 hours, cooled, 400 ml of water was added, the mixture was acidified with 6N hydrochloric acid and extracted with ether. The extract was stripped of solvent, and the residue was recrystallized from benzene to give ethyl (2-nitrophenyl)glyoxylate oxime (3A), as a white solid, m.p.: 167°–168° C.

20 g of 3A was dissolved in 100 ml of diglyme and the solution was added dropwise to a vigorously stirred mixture of 2.5 g of sodium hydride and 100 ml of diglyme, under nitrogen at room temperature. The mixture was heated slowly to and held at 150° C. for 6 hours, then cooled, mixed with 200 ml of water and extracted with ether. The extract was dried and stripped of solvent. The residue was distilled in a Kugelrohr apparatus (60° C./0.05 Torr); the resulting residue was dissolved in warm petroleum ether, the solution was chilled to 0° C., and the solid phase was collected and dried, to give ethyl 3-benzisoxazolylcarboxylate (3B), as a white solid, m.p.: 53°–55° C.

8.6 g of 3B was mixed with 175 ml of 70% sulfuric acid and the mixture was heated at 80° C. for 4 hours. The mixture was cooled, 200 ml of cold water was added, the mixture was extracted with ether, and the extract was dried (Na$_2$SO$_4$) and stripped of solvent. The residue was triturated with pentane, and the solid was collected and dried to give 3-benzisoxazolecarboxylic acid (3C), as a white solid, m.p.: 132°–134° C. (with decomposition).

3 was prepared, as a white solid, m.p. 225.5°–228° C., from 3C, by procedures described in Example 1 for preparing 1 from 1B.

EXAMPLE 4

Dimethyl 2-methyl-5-(5-methyl-4-oxazolyl)pyrrole-3,4-dicarboxylate (4)

A stirred mixture of 10.0 g of methyl isocyanoacetate, 15.1 g of 1,8-diazabicyclo[5.4.0]undec-7-ene (DBU) and 133 ml of anhydrous THF was cooled to 0° C., and a solution of 10.2 g of acetic anhydride in 33 ml of THF was added dropwise over 15 minutes. The mixture was stirred overnight at room temperature and stripped of solvent. The residue was mixed with 250 ml of ethyl acetate, the mixture was washed with water, dried (MgSO$_4$), filtered and stripped of solvent. The residue was chromatographed on silica gel with a 1:1 v:v ethyl acetate/hexane mixture as eluent. The middle fractions gave methyl 5-methyl-4-oxazolecarboxylate (4A) as a white solid, m.p.: 46.5°–47.0° C.

4 was prepared, as a yellow solid, m.p.: 152°–154.5° C., from 4A by the procedures described in Example 2 for preparing 2 from 2B.

EXAMPLE 5

Dimethyl 2-methyl-5-(5-methyl-2-oxazolyl)-pyrrole-3,4-dicarboxylate (5)

A mixture of 37.5 g of glycine, 243 ml of pyridine and 550 ml of acetic anhydride was heated at reflux for 2 hours, then was stripped under reduced pressure. The residue was distilled in a Vigreaux column to give a product boiling at 93°–95° C./0.5 Torr., identified as N-acetonyldiacetamide (5A).

A mixture of 41.0 g of 5A, 140 ml of water and 140 ml of concentrated hydrochloric acid was heated at reflux for 3 hours, then stripped of volatiles under reduced pressure (bath temperature 60° C.). The residue was mixed with 130 ml of benzene, 117 g of methyl oxalyl chloride was added over 10 minutes, then the mixture was heated at reflux for 2 hours, cooled and stripped of solvent. The residue was neutralized with 3N aqueous sodium carbonate solution, and the mixture was extracted with methylene chloride. The extract was dried, filtered and stripped of solvent. 32 g of the residue was mixed with 28.3 ml of phosphorus oxychloride, 83.4 ml of triethylamine and 1.5 liters of toluene and the mixture was stirred at 80° C. for 20 hours. The mixture was cooled and stripped of solvent. The residue was dissolved in 500 ml of water, the solution was extracted with methylene chloride, and the extract was dried and stripped of solvent. The residue was chromatographed on silica gel with a 1:4 v:v ethyl acetate/hexane mixture as eluent. The middle fractions gave a yellow solid, m.p.: 45°–47.5° C., identified as methyl 5-methyl-2-oxazolecarboxylate (5B).

5 was prepared, as a light orange solid, m.p.: 213.5°–215° C., from 5B, by the procedures described in Example 2 for preparing 2 from 2B.

EXAMPLE 6

Diethyl 2-methyl-5-(2-pyridinyl)pyrrole-3,4-dicarboxylate (6)

5.75 g of sodium was treated with 100 ml of ethanol, the unreacted ethanol was stripped and the solid sodium ethoxide was dried by azeotroping with benzene. The sodium ethoxide was mixed with 150 ml of benzene, the mixture was stirred and heated to reflux and a mixture of 25 g of ethyl picolinate and 32.3 ml of ethyl acetate was added dropwise over 15 minutes. Then the mixture was stirred for 30 minutes and cooled. After 150 ml of water was added, glacial acetic acid was added until the mixture was acidic. The two liquid phases were separated. The organic phase was dried (Na$_2$SO$_4$), stripped of solvent and distilled in a Kugelrohr apparatus to give ethyl 3-(2-pyridinyl)-3-oxopropanoate (6A), as a light yellow oil, b.p.: 95°–110°/0.05 Torr.

6A also was prepared as follows: 73 ml of diethyl carbonate was added to a mixture of 30 g of hexane-washed sodium hydride and 150 ml of benzene, and the resulting mixture was heated at reflux temperature for 30 minutes, when 33 ml of 2-acetylpyridine was added dropwise over 60 minutes. The mixture was cooled to room temperature, 75 ml of glacial acetic acid and 250 ml of water were added, and the mixture was extracted with diethyl ether. The extract was dried, stripped of solvent and the residue was distilled in a Kugelrohr apparatus to give 6A.

54 g of sodium methoxide was dissolved in a mixture of 100 ml of methanol and 100 ml of tetrahydrofuran (THF). 50 grams of aluminum oxide (activated, neutral, Brockman I, Aldrich) was added and the mixture was stirred for 30 minutes. The solvents were removed under reduced pressure to give aluminum oxide-supported sodium methoxide (6B).

A solution of 9.7 g of 6A was dissolved in 15 ml of THF and added to 5.5 g of 6B. The mixture was stirred at room temperature for 30 minutes, then the solvent was evaporated under reduced pressure. 13.86 g of ethyl 2-chloroacetoacetate was added to the residue, the mixture was stirred for 90 hours at room temperature, then mixed with 200 ml of methylene chloride. The resulting mixture was filtered, the filtrate was stripped of solvent in a Kugelrohr apparatus at 80°–85° C./0.05 Torr. The residue was dissolved in 50 ml of acetic acid, 12.0 g of ammonium acetate was added and the mixture was heated at 100° C. for 2 hours. After cooling, 200 ml of water was added, the mixture was extracted with methylene chloride, the extract was stripped of solvent and the residue was concentrated in a Kugelrohr apparatus at 50° C./0.05 Torr to remove acetic acid. The residue was dissolved in 100 ml of methylene chloride, 20 g of silica gel was added to the solution, the solvent was evaporated, and the residue was flash chromatographed on silica gel with a 3:2 v:v mixture of hexane and ethyl acetate as eluent. Work-up of the later fractions gave 6, as a light yellow solid, m.p.: 96°–100° C.

EXAMPLE 7

Dimethyl 2-methyl-5-(2-pyridinyl)pyrrole-3,4-dicarboxylate (7)

Method A 51 ml of dimethyl carbonate was added to a mixture of 30 g of pentane-washed sodium hydride in 150 ml of benzene and the mixture was stirred and heated at reflux for 30 minutes. Then a solution of 36 g of 2-acetylpyridine in 50 ml of benzene was added dropwise over 1 hour. 150 ml of THF was added to facilitate stirring, the mixture was stirred and heated for a further 1 hour, and cooled to room temperature. A mixture of 250 ml of water and 75 ml of glacial acetic acid was added dropwise while the mixture was cooled to hold its temperature to about 15° C. Two liquid liquid layers formed; the upper layer was separated, dried (Na$_2$SO$_4$) and stripped of solvents. The residue was distilled in a Kugelrohr apparatus at 110°–115° C./0.05 Torr., to give methyl 3-(2-pyridinyl)-3-oxopropanoate (7A), as a yellow oil.

7 was obtained, as a light yellow solid, by treating 7A according to the procedures described in Example 6 for preparing 6 from 6A.

Method B 7 also was obtained, as a white solid, as follows:

A solution of 25 ml of methyl 2-chloroacetoacetate in 25 ml of THF was added dropwise over 30 minutes to a solution of 37.5 g of tosyl hydrazine in 150 ml of THF. The mixture was allowed to stand overnight, then heated at reflux for 2 hours, cooled to room temperature and stripped of solvent. The residue was then dissolved in 200 ml of ether. Crystallization occurred at room temperature. The collected solids were dried to give methyl 2-chloro-3-(tosylhydrazono)butanoate (7B), as a light yellow solid, m.p.: 97°–101° C.

0.46 g of sodium was treated with 30 ml of methanol, then a solution of 3.2 g of 7A in 30 ml of THF was added and the mixture was stirred for 15 minutes. 30 ml of THF was added, then a solution of 6.4 g of 7B in 30 ml of THF was added drop by drop and the mixture was stirred at room temperature for 1 hour. The solvents were evaporated, the residue was dissolved in 75 ml of water and the solution was extracted with methylene chloride. The extract was dried ($Na_2SO_4$) and stripped of solvent. The residue was dried, then flash chromatographed on silica gel with a 9:1 v:v mixture of methylene chloride and methanol as eluent, to give dimethyl 2-(1-tosylhydrazono)ethyl)-3-((2-pyridinyl)-carbonyl)-1,4-butanedioate (7C), as a white solid, m.p.: 70°–90° C.

For 5 minutes, hydrogen chloride gas was bubbled into a solution of 3.2 g of 7C in 50 ml of methanol, then the mixture was heated at reflux for 1 hour, cooled, and stripped of solvent. The residue was mixed with 100 ml of a 1:1 v:v mixturre of water and methylene chloride and neutralized by shaking the mixture with solid sodium bicarbonate. The methylene chloride layer was separated, dried ($Na_2SO_4$) and stripped of solvent. The residue was dissolved in a minimum amount of methylene chloride, 100 ml of a 1:1 v:v mixture of ether and pentane was added, and the mixture was allowed to stand overnight. The mixture was filtered, and the collected solids were dried, to give dimethyl 2-methyl-1-(tosylamino)-5-(2-pyridinyl)pyrrole-3,4-dicarboxylate (7D), as a solid, m.p.: 145°–147° C.

A solution of 0.443 g of 7D in 30 ml of methanol was added to a mixture of 1 g of Raney nickel in 20 ml of methanol. The mixture was heated at reflux for 3 hours, cooled and extracted with hot methanol. The extract was concentrated to about 5 ml, dissolved in water acidified to pH=2 with hydrochloric acid, and the solution was neutralized with solid sodium bicarbonate to pH=7. The mixture was extracted with methylene chloride, the extract was dried ($Na_2SO_4$), and stripped of solvent, and the residue was flash chromatographed on silica gel with a 9:1 v:v mixture of methylene chloride and ethyl acetate as solvent. The later fractions gave 7.

EXAMPLE 8

4-Ethyl 3-methyl-2-methyl-5-(2-pyridinyl)pyrrole-3,4-dicarboxylate (8)

1.25 g of pentane-washed sodium hydride was suspended in 50 ml of ether, then a solution of 10 g of 6A in 100 ml of ether was added dropwise over 20 minutes. The resulting mixture was stirred at room temperature for 20 minutes, giving mixture 8A.

A solution of 5.97 g of methyl acetoacetate in 100 ml of ether was added dropwise over 20 minutes to a mixture of pentane-washed sodium hydride in 50 ml of ether, and the mixture was stirred at room temperature for 20 minutes. The resulting mixture was added to 8A, stirred at reflux for 30 minutes, and cooled to room temperature. 12.25 g of iodine in 200 ml of ether was added dropwise over 30 minutes to the stirred mixture and the mixture was stirred overnight at 35° C. The mixture was cooled to room temperature and 200 ml of water was added. The ether layer was separated, dried and stripped of solvent, the residue being 8B. The aqueous phase was neutralized with 1N hydrochloric acid and extracted with methylene chloride. The extract was dried ($Na_2SO_4$) and stripped of solvent. The residue was mixed with ether and the mixture was filtered. The filtrate was stripped of solvent and the residue was combined with 8B to give 8C.

12.5 g of 8C, 15 g of ammonium acetate and 100 ml of glacial acetic acid were mixed and the mixture was heated at reflux for 2 hours. Then 200 ml of water was added and the resulting mixture was extracted with methylene chloride. The extract was stripped of solvent and the residue was flash chromatographed on silica gel, with a 7:3 v:v mixture of hexane and ethyl acetate as eluent. The second fraction that was obtained gave 8, as a white solid, m.p.: 96°–97° C.

EXAMPLE 9

3-Ethyl 4-methyl-2-methyl-5-(2-pyridinyl)pyrrole-3,4-dicarboxylate (9)

9 was prepared, as a light yellow solid, m.p.: 75°–80° C. (with decomposition), by treating 7A by the procedures described in Example 8 for preparing 8 from 6A, except that methyl acetoacetate was used instead of ethyl acetoacetate.

EXAMPLE 10

Dimethyl 2-methyl-5-(3-chloro-2-pyridinyl)pyrrole-3,4-dicarboxylate (10)

At room temperature, 258.9 g of (85%) m-chloroperoxybenzoic acid was added in portions over 20 minutes to a stirred solution of 150 g of 3-chloropyridine in one liter of methylene chloride, the mixture being cooled to hold its temperature below 35° C. Then the mixture was stirred at room temperature for 2 days, washed with a 25% aqueous solution of potassium carbonate, dried ($MgSO_4$) and stripped of volatiles. The product was triturated with ether at −78° C., then stripped of solvent to give the N-oxide (10A), as a white solid, m.p.: 51.5°–55° C.

125 g of trimethylsilyl cyanide was added to a stirred mixture of 54.3 g of 10A, 85 g of triethylamine and 420 ml of acetonitrile at room temperature. The mixture was heated at reflux for 4 hours, cooled and stripped of volatiles under reduced pressure. 3N aqueous sodium carbonate solution was added until the mixture was basic then the mixture was extracted with methylene chloride. The extract was dried ($MgSO_4$), and stripped of solvent. The residue was chromatographed on silica gel with a 1:3 v:v mixture of ethyl acetate and hexane as eluent, to give 3-chloro-2-cyanopyridine (10B), as an off-white solid, m.p.: 80.5°–83° C.

64.1 g of 10B was refluxed in 460 ml of 2N aqueous sodium hydroxide solution for 1 hour. The mixture was cooled, acidified to pH=2.5 with concentrated hydrochloric acid, stripped of water under reduced pressure, then azeotroped with methanol. The residue was stirred with 250 ml of a 1:1 v:v mixture of methylene chloride and methanol, and the resulting mixture was filtered. The filtrate was stripped of volatiles (water bath temperature 60° C). This purification procedure was repeated, to give 3-chloropicolinic acid (10C), as a yellow solid, m.p.: 125.5°–127.5° C.

6.3 ml of concentrated hydrochloric acid was added to a solution of 20 g of 10C in 400 ml of methanol and the mixture was heated at reflux for 6 hours. The mixture was cooled and stripped of methanol. The residue was treated with an aqueous sodium bicarbonate solution and extracted with methylene chloride. The extract was washed with saturated sodium chloride solution, dried (MgSO$_4$) and stripped to give the methyl ester (10D) of 10C, as a brown oil.

66 g of 10D and 84.5 g of methyl acetate were added to 22.2 g of hexane-washed sodium hydride. Some reaction occurred immediately and after 5 minutes the mixture reacted vigorously. When the reaction subsided, the mixture was quenched in one liter of ice water in a nitrogen atmosphere, acidified with acetic acid and filtered. The filtrate was extracted with methylene chloride, and the extract was dried (MgSO$_4$) filtered and stripped of solvent. The residue was chromatographed on silica gel with methylene chloride as eluent, to give methyl 3-(3-chloro-2-pyridinyl)-3-oxopropanoate (10E), as a pale yellow oil.

10 was prepared, as a white solid, m.p.: 113°–115.5° C., by treating 10E according to the procedures described in Example 2 for preparing 7 from 7A by Method B.

EXAMPLES 11–25

The following individual species of Formula I, wherein R and R$^1$ each is methyl, R$^2$ is hydrogen, J=J-5 and each of R$^7$, R$^8$ and R$^9$ not mentioned was hydrogen, were prepared by the procedures described in the stated Example.

| Species | R$^7$, R$^8$, R$^9$ | Procedure of Example | Physical Properties, melting point, °C. |
|---|---|---|---|
| 11 | R$^9$ = ethyl | 6 | Light orange solid, 115–116.5 |
| 12 | R$^9$ = C | 6 | Yellow solid, 119.5–121.5 |
| 13 | R$^7$ = (F$_2$HCO—) | 6 | Yellow solid, 131–133 |
| 14 | R$^7$ = methyl | 6 | White solid, 87.5–91 (with decomposition) |
| 15 | R$^9$ = I | 6 | Orange semisolid, 53–114 |
| 16 | R$^7$ = I | 6 | Off-white solid, 139–147 |
| 17 | R$^8$ = Cl | 6 | Light yellow solid, 124.5–128 |
| 18 | R$^8$ = methoxy | 6 | Yellow solid, 135–138 |
| 19 | R$^7$ = F | 7B | Light green solid, 120.5–125.5 |
| 20 | R$^7$ = Cl, R$^9$ = Cl | 7B | Off-white solid, 180–182.5° C. |
| 21 | R$^7$ = methoxy, R$^9$ = Cl | 7B | Off-white solid, 168–169.5° C. |
| 22 | R$^7$ = methoxy | 7B | Off-white solid, 150–152.5° C. |
| 23 | R$^8$ = methyl | 7B | White solid, 135.5–139° C. |
| 24 | R$^8$ = tert-butyl | 7B | White solid, 123.5–124° C. |
| 25 | R$^9$ = dimethoxymethyl | 6 | Brown oil |

EXAMPLE 26

Dimethyl 2-methyl-5-(4-methylthio)-2-pyridinyl)pyrrole-3,4-dicarboxylate (26)

0.10 g of sodium methylmercaptide was added to a solution of 0.17 g of 17 in 5 ml of dimethylformamide at room temperature. The mixture was stirred at 80° C. overnight, cooled and poured into 10 ml of water. The mixture was acidified with glacial acetic acid and extracted with methylene chloride. The extract was dried (Na$_2$SO$_4$) and stripped of solvent. The residue was flash chromatographed on silica gel with a 5:95 v:v mixture of ethyl acetate and methylene chloride as eluent. The later fractions were stripped of eluent, the residue was recrystallized from ether at −78° C., and the product was dried under reduced pressure to give 26, as on off-white solid, m.p.: 140°–142.5° C.

EXAMPLE 27

Dimethyl 1-((((methoxymethyl)carbonyl)oxy)methyl)-2-methyl-5-(2-pyridinyl)pyrrole-3,4-dicarboxylate (27)

A solution of 22.9 g of N,N'-dicyclohexylcarbodiimide in 150 ml of anhydrous ether was added to a stirred solution of methoxyacetic acid at room temperature. The temperature of the mixture rose to 31° C. After 2 hours of stirring, the mixture was filtered and the filtrate was stripped of solvent. The residue was cooled to 0° C. and filtered, to give the anhydride of methoxyacetic acid (27A), as a yellow oil.

A mixture of 0.79 g of 7, 1.64 g of 27A and 0.17 g of paraformaldehyde was heated at 120° C. for 2.5 hours. The mixture was cooled to room temperature and distilled in a Kugelrohr apparatus to remove anhydride and methoxyacetic acid and the residue was chromatographed on silica gel, with a 1:4 v:v mixture of ether and methylene chloride as eluent. The later fractions gave 27, as light-green oil.

EXAMPLE 28

Dimethyl 2-methyl-5-(2-pyrazinyl)pyrrole-3,4-dicarboxylate (28)

Sodium methoxide (prepared by treating 14.0 g of sodium with 100 ml of methanol, then removing the excess methanol) was suspended in 500 ml of benzene and the mixture was heated to reflux. Then a mixture of 53.6 g of the methyl ester of 2-pyrazinecarboxylic acid and 59.2 g of methyl acetate in 100 ml of benzene was added over 15 minutes to the stirred mixture. The mixture was stirred for 30 minutes, cooled, 400 ml of water was added, then 120 ml of glacial acetic acid was added, the mixture was shaken, then allowed to stand. The organic phase was separated, dried (Na$_2$SO$_4$) and stripped of solvent. The residue was mixed with 400 ml of ether, the mixture was warmed, then allowed to cool to room temperature and filtered, to give methyl 3-(2-pyrazinyl)-3-oxopropionate (28A), as a solid, m.p.: 109°–110° C.

5.4 g of 6B was added to a solution of 7.16 g of 28A in 25 ml of THF, the mixture was stirred at 40° C. for 45 minutes, then stripped of solvent. 9.8 g of methyl 2-chloroacetoacetate was added to the residue and the mixture was held at room temperature for 5 days. Then it was mixed with 200 ml of methylene chloride, the mixture was filtered and stripped of volatiles. The residue was flash chromatographed on silica gel, with a 3:2 v:v mixture of hexane and ethyl acetate as eluent. 0.294 g of the product (a solid, m.p.: 110°–120° C.) was dissolved in 10 ml of methanol, then 0.154 g of ammonium acetate and 1 drop of glacial acetic acid were added. The mixture was heated at reflux for 2 hours, then stripped of volatiles. The residue was mixed with water, the mixture was extracted with methylene chloride, the extract was dried (Na$_2$SO$_4$) and stripped of solvent. The residue was mixed with 15 ml of ether, the mixture was held at room temperature for 10 minutes, then filtered, to give 28, as a light yellow solid, m.p.: 154°–155° C.

EXAMPLES 29 AND 30

By the procedures described in Example 28 (using ethylacetate and sodium ethoxide), diethyl 2-methyl-5-(2-pyrazinyl)pyrrole-3,4-dicarboxylate (29), was prepared as a brown solid, m.p.: 96°–98° C., and 4-ethyl 3-methyl 2-methyl-5-(2-pyrazinyl)pyrrole-3,4-dicarboxylate (30), was prepared, as a solid, m.p.: 101°–102° C. (from the ethyl ester of 2-pyrazinecarboxylic acid).

EXAMPLE 31

Dimethyl 2-methyl-5-(3-methyl-2-pyrazinyl)pyrrole-3,4-dicarboxylate (31)

21.4 g of dimethyl carbonate was added dropwise to a stirred mixture of 5.7 g of sodium hydride and 100 ml of toluene at room temperature. Then the mixture was heated to 80° C. and a solution of 16.1 g of 2-acetyl-3-methylpyrazine in 75 ml of toluene was added dropwise and the mixture was stirred at 75° C. for one hour. The mixture was cooled, 100 ml of water was added and the mixture was acidified with glacial acetic acid. The organic phase was separated, dried (Na$_2$SO$_4$) and stripped of volatiles. The residue was flash chromatographed on silica gel, with a 9:1 v:v mixture of methyl chloride and ethyl acetate as eluent. The second set of fractions was stripped of solvent to give methyl 3-(3-methyl-2-pyrazinyl)-3-oxopropionate (31A), as a yellow oil.

0.81 g of sodium was heated with 20 ml of methanol, then a solution of 6.8 g of 31A in 20 ml of methanol was added and the mixture was stirred at room temperature for 1 hour. Then a solution of 11.2 g of 7B in 25 ml of THF was added, and the mixture was stirred at room temperature for 2 hours. The mixture was stripped of volatiles, 100 ml of methanol was added to the residue and hydrogen chloride gas was bubbled through the mixture, which then was heated at reflux for 2 hours. The mixture was cooled, neutralized with a saturated aqueous solution of sodium bicarbonate and extracted with methylene chloride. The extract was stripped of volatiles, and the residue was triturated with 10 ml of ether. The solid product was collected and dried (Na$_2$SO$_4$) to give dimethyl 2-methyl-1-(tosylamino)-5-(3-methyl-2-pyrazinyl)pyrrole-3,4-dicarboxylate (31C), as a light yellow solid, m.p.: 177°–178° C.

A solution of 4.57 g of 31C in 20 ml of methanol was added to a mixture of 15 g of Raney nickel in 30 ml of methanol. The mixture was heated at reflux overnight, cooled and the methanol phase was decanted. The catalyst was washed with 100 ml of 1:1 mixture of methylene chloride and methanol. The washings were combined with the methanol phases, and the resulting mixture was stripped of the solvents. The residue was dissolved in a mixture of 20 ml of water and 100 ml methylene chloride. The mixture was acidified to pH=2 with 6N hydrochloric acid, and the solution was neutralized with solid sodium bicarbonate to pH=7. The organic phase was separated, dried (Na$_2$SO$_4$), and stripped of solvent, and the residue was flash chromtographed on silica gel, with a 7:3 v:v mixture of methylene chloride and ethyl acetate as solvent. The product was triturated with ether and the solid product was collected to give 31, as a white solid, m.p.: 155°–156° C.

EXAMPLE 32

Dimethyl 2-methyl-5-(4-pyrimidinyl)pyrrole-3,4-dicarboxylate (32) was prepared, as a light yellow solid, m.p.: 210°–211° C., from the methyl ester of 4-pyrimidinecarboxylic acid by the procedures described in Example 28 for preparing 28 from the methyl ester of 2-pyrazinecarboxylic acid.

EXAMPLE 33

Dimethyl 2-methyl-5-(5-chloro-4-pyrimidinyl)pyrrole-3,4-dicarboxylate (33) was prepared as a white solid, m.p.: 180°–181° C., from the methyl ester of 5-chloro-4-pyrimidinecarboxylic acid by the procedures described in Example 28 for preparing 28 from the methyl ester of 2-pyrazinecarboxylic acid.

EXAMPLE 34

Dimethyl 2-methyl-5-(2-pyrimidinyl)pyrrole-3,4-dicarboxylate (34) was prepared, as an orange solid, m.p.: 140°–146° C., from the methyl ester of 2-pyrimidinecarboxylic acid, according to the procedure described in Example 28 for preparing 28 from the methyl ester of 2-pyrazinecarboxylic acid.

EXAMPLES 35 AND 36

4-N-oxide of 28 (i.e., 35) and 3-N-oxide of 33 (i.e., 36)

0.28 g of meta-chloroperoxybenzoic acid was added to a solution of 0.39 g of 28 in 15 ml of methylene chloride at 5° C., then the mixture was stirred at room temperature overnight. The solvent was stripped and the residue was flash chromatographed on silica gel, with a 3:2 v:v mixture of methylene chloride and ethyl acetate as eluent. 35 was obtained, as white solid, m.p.: 200°–205° C., from the last set of fractions obtained from the elution.

33 was treated in a like manner, to give 36, as a light brown solid, m.p.: 170°–171° C. (with decomposition).

EXAMPLE 37

Dimethyl 5-methyl-2-(1-methyl-2-imidazolyl)pyrrole-3,4-dicarboxylate (37)

in a nitrogen atmosphere, 41.0 g of 1-methylimidazole was added to 500 ml of acetonitrile, followed by 70 ml of triethylamine, and the mixture was cooled in an ice bath. 38.63 g of methyl chloroformate was added dropwise over 30 minutes, the mixture was stirred at room temperature overnight, and filtered. The filtrate was stripped of volatiles; the residue was dissolved in 500 ml of methylene chloride and the solution was washed with brine, then water, then dried (Na$_2$SO$_4$) and stripped of solvent. The residue was flash chromatographed on silica gel, with a 975:25 v:v mixture of methylene chloride and methanol as eluent. Evaporation of the solvent gave methyl 1-methylimidazole-2-carboxylic acid (37A), as a light yellow oil.

Dry sodium methoxide (prepared by treating 5:1 g of sodium with 50 ml of methanol, then evaporating the methanol), was mixed with 50 ml of benzene and the mixture was heated to reflux while a mixture of 16.0 g of 37A, 14 ml of methyl acetate and 50 ml of benzene was added over 5 minutes. The mixture was heated at reflux for one hour, then cooled; 200 ml of water and 25 ml of glacial acetic acid were added. The benzene phase was separated, dried (Na₂SO₄) and stripped of solvent. The residue was distilled to 20° C. and 0.05 Torr. in a Kugelrohr apparatus to give methyl 3-(1-methyl-2-imidazolyl)-3-oxopropionate (37B), as an oil.

3.5 g of 6B was added to a stirred mixture of 5.66 g of 37B and 10 ml of THF, and the mixture was stirred at room temperature for 30 minutes. The mixture was stripped of THF, 7.2 ml of methyl 2-chloroacetoacetate was added and the mixture was stirred at room temperature for 4 days. Then 10 ml of methylene chloride was added, the mixture was filtered and the filtrate was distilled to 60° C./0.05 Torr. in a Kugelrohr apparatus. The product was mixed with 4.8 g of ammonium acetate and 15 ml of acetic acid, the mixture was heated at reflux for 1 hour, and cooled. 200 ml of water was added and the mixture was extracted with methylene chloride. The extract was dried and stripped of solvent. The residue was chromatographed on silica gel, with a 3:2 v:v mixture of hexane and ethyl acetate as eluent, then with a 1:9 v:v mixture of methanol and methylene chloride as eluent. The product from this latter elution was stripped of solvent and the residue was flash chromatographed on silica gel, with a 95:5 v:v mixture of methylene chloride and methanol as eluent, to give 37, as a brown solid, m.p.: 142°–143° C.

EXAMPLE 38

Dimethyl 5-methyl-2-(1-methyl-4-imidazolyl)pyrrole-3,4-dicarboxylate (38)

0.31 g of 2-acetamidoacrylic acid was stirred in 200 ml of 40% methylamine in water at 40° C. for 80 hours. Excess methylamine and water were evaporated under reduced pressure, and the residue was held under high vacuum overnight. The residue was recrystallized from a 1:1 v:v mixture of ether and methanol and dried to give 2-acetylamino-3-(methylamino)propionic acid (38A) as a white solid, m.p.: 166.5°–168.5° C. (with decomposition).

27 g of 38A was refluxed in 500 ml of 25N hydrochloric acid for 2 hours, then volatiles were removed under reduced pressure and the residue was dehydrated by azeotroping with ethanol, then holding the residue under reduced pressure at 40° C. over a weekend, to give a white highly hydroscopic solid (38B), m.p.: 85°–91° C.

A mixture of 31 g of 38B, 31 g of triethyl orthoformate and 20 ml of concentrated hydrochloric acid was heated at 90°–100° C. for 35 hours, volatile by-product being continuously removed as vapor, then filtered. The collected solid was recrystallized from ethanol/ether to give 1-methylimidazoline-4-carboxylic acid hydrochloride (38C), as a light gray-brown solid, m.p.: 186°–189° C. (with decomposition).

17.0 g of 38C was dissolved in 203 ml of anhydrous methanol and dry hydrogen chloride was bubbled rapidly into the mixture while it was heated to and at reflux for 2 hours. the mixture was cooled, stripped of volatiles, mixed with 300 ml of water, neutralized with solid sodium bicarbonate, made basic to pH=9 with 3N aqueous sodium carbonate solution. The aqueous phase was extracted with methylene chloride, the extract was dried (MgSO₄), filtered and stripped of solvent, to give methyl 1-methylimidazoline-4-carboxylate (38D), as a brown oil.

19.0 g of manganese dioxide was added to a stirred solution of 4.7 g of 38D in ethanol-free, chloroform and the mixture was stirred overnight at room temperature. The mixture was heated at reflux for 1 hour, cooled, 9.5 g of manganese dioxide was added; the mixture was stirred at room temperature for 2 hours and at reflux for 30 minutes. The mixture was cooled and filtered and the filtrate was stripped of solvent to give methyl 1-methylimidazole-4-carboxylate (38E), as a yellow solid, m.p.: 72.5°–81° C.

38 was obtained, as an orange solid, melting point not determined, by treating 38E by the procedures described in Example 37 for preparing 37 from 37A.

EXAMPLE 39

Dimethyl 5-methyl-2-(1,5-dimethyl-3-pyrazolyl)pyrrole-3,4-dicarboxylate (39)

9.2 ml of methylhydrazine was added dropwise over 30 minutes to a solution of 25 g of ethyl 2,4-dioxovalerate in 36 ml of ethanol, the temperature of the mixture being kept below 40° C. by cooling in an ice bath. The resulting solution was heated at reflux for 23 hours, poured into 300 ml of ice water and the resulting mixture was extracted with ether. The extract was dried (MgSO₄), filtered and stripped of solvent. The residue was chromatographed on silica gel, with a 1:1 v:v mixture of ethyl acetate and hexane as eluent. The middle fractions gave ethyl 1,5-dimethylpyrazole-3-carboxylate (39A), as a yellow oil.

39A was converted to 39, obtained as a light orange solid, m.p.: 153°–154.5° C., by the procedures described in Example 37 for converting 37A to 37.

The compounds within Tables 1 through 7 can be prepared by the methods taught in Example 1 through Example 39.

TABLE 1

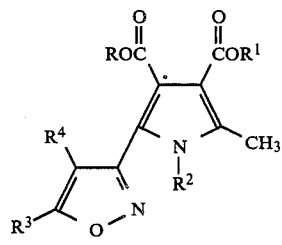

| R | R¹ | R² | R³ | R⁴ | m.p. (°C.) |
|---|----|----|----|----|------------|
| CH₃ | CH₃ | H | CH₃ | CH₃ | |
| CH₃ | CH₃ | H | C₂H₅ | CH₃ | |
| CH₃ | CH₃ | $\underset{\text{CH}_2\text{OCCH}_3}{\overset{\overset{\text{O}}{\|}}{}}$ | C₂H₅ | CH₃ | |
| CH₃ | CH₃ | H | CH₂—CH₂—CH₂ | | |
| CH₃ | CH₃ | $\underset{\text{CH}_2\text{OCCH}_2\text{OCH}_3}{\overset{\overset{\text{O}}{\|}}{}}$ | CH₂—CH₂—CH₂ | | |
| CH₃ | CH₃ | H | CH₂—CH₂—CH₂—CH₂ | | |
| CH₃ | CH₃ | H | C₆H₅ | CH₃ | |

TABLE 2

Structure: Pyrrole with ROC(=O) and R¹OC(=O) groups at 3,4-positions, CH₃ at 2-position, R² on N, and oxazole substituent at 5-position with R⁵ group.

| R | R¹ | R² | R⁵ | m.p.(°C) |
|---|---|---|---|---|
| CH₃ | CH₃ | H | C₂H₅ | |
| CH₃ | CH₃ | CH₂OC(=O)CH₂Cl | C₂H₅ | |
| C₂H₅ | CH₃ | H | CH₃ | |
| CH₃ | CH₃ | H | C₆H₅ | |
| CH₃ | CH₃ | H | C₆H₅CH₂ | |
| CH₃ | CH₃ | H | CH₂OCH₃ | |
| CH₃ | CH₃ | H | CH₂OC₂H₅ | |
| CH₃ | CH₃ | H | CH₂SCH₃ | |

TABLE 3

Structure: Pyrrole with ROC(=O) and R¹OC(=O) groups, CH₃ at 2-position, R² on N, and pyridine substituent with R⁷, R⁸, R⁹ groups.

| R | R¹ | R² | R⁷ | R⁸ | R⁹ | m.p. (°C) |
|---|---|---|---|---|---|---|
| CH₃ | CH₃ | H | C₂H₅ | H | H | 130–131 |
| CH₃ | CH₃ | H | CH₃ | CH₃ | H | |
| CH₃ | CH₃ | CH₂OC(=O)CH₃ | CH₃ | CH₃ | H | |
| CH₃ | CH₃ | H | Cl | H | CF₃ | |
| CH₃ | CH₃ | H | H | H | OCH₃ | |
| CH₃ | CH₃ | H | Cl | H | OCH₃ | |
| CH₃ | CH₃ | H | OCH₃ | CH₃ | H | gum |
| CH₃ | CH₃ | H | H | CN | H | |
| CH₃ | CH₃ | H | CH₂OH | H | H | |
| CH₃ | CH₃ | H | CH₂OCH₃ | H | H | |
| CH₃ | CH₃ | H | CH₃ | H | CH₃ | |
| Et | CH₃ | H | CH₃ | CH₃ | H | |
| CH₃ | CH₃ | H | Cl | OCH₃ | Cl | |
| CH₃ | CH₃ | H | SCH₃ | H | H | |
| CH₃ | CH₃ | H | C₆H₅CH₂ | H | H | |
| CH₃ | CH₃ | H | CF₃CH₂O | H | H | |

TABLE 4

Structure: Pyrrole with ROC(=O) and R¹OC(=O) groups, CH₃ at 2-position, R² on N, and pyrazine substituent with R¹⁰ group.

| R | R¹ | R² | R¹⁰ | m.p. (°C) |
|---|---|---|---|---|
| CH₃ | CH₃ | CH₂OC(=O)CH₃ | H | |
| CH₃ | CH₃ | H | C₂H₅ | |
| CH₃ | CH₃ | CH₂OC(=O)CH₃ | C₂H₅ | |
| CH₃ | CH₃ | H | Cl | |
| CH₃ | CH₃ | H | CH₃ | 155–156 |

TABLE 5

Structure: Pyrrole with ROC(=O) and R¹OC(=O) groups, CH₃ at 2-position, R² on N, and pyrimidine substituent with R¹¹ group.

| R | R¹ | R² | R¹¹ | m.p.(°C) |
|---|---|---|---|---|
| CH₃ | CH₃ | H | CH₃ | |
| CH₃ | CH₃ | CH₂OC(=O)CH₃ | H | |
| CH₃ | CH₃ | H | C₂H₅ | |
| CH₃ | CH₃ | H | C₆H₅ | |

TABLE 6

Structure: Pyrrole with ROC(=O) and R¹OC(=O) groups, CH₃ at 2-position, R² on N, and pyrazole substituent with R¹⁴, R¹⁵, R¹⁶ groups.

| R | R¹ | R² | R¹⁴ | R¹⁵ | R¹⁶ | m.p. (°C) |
|---|---|---|---|---|---|---|
| CH₃ | CH₃ | H | CH₃ | CH₃ | CH₃ | |
| CH₃ | CH₃ | H | CH₃ | C₂H₅ | CH₃ | |
| CH₃ | CH₃ | H | C₂H₅ | CH₃ | H | |
| CH₃ | CH₃ | H | C₆H₅ | CH₃ | H | |
| CH₃ | CH₃ | H | CH₃ | —CH₂CH₂CH₂— | | |
| CH₃ | CH₃ | H | CH₃ | —CH₂CH₂CH₂CH₂— | | |
| CH₃ | CH₃ | CH₂OC(=O)CH₃ | CH₃ | —CH₂CH₂CH₂— | | |

TABLE 7

Structure: pyrrole with ROC(=O) and R¹OC(=O) substituents at 3,4-positions, J at 5-position, CH₃ at 2-position, R² on N.

| R | R¹ | R² | J | m.p.(°C) |
|---|----|----|---|----------|
| CH₃ | CH₃ | H | thiazole (S,N ring) substituent | |
| CH₃ | CH₃ | H | 5-chloro-benzisoxazol-3-yl | |
| CH₃ | CH₃ | CH₂OC(=O)CH₃ | 2-methyl-isoxazol-5-yl (with CH₃) | |
| CH₃ | CH₃ | H | 2-phenyl-isoxazol-5-yl (with C₆H₅) | |
| CH₃ | CH₃ | H | 4-chloro-pyrimidin-2-yl | 180–181 |
| CH₃ | CH₃ | H | 1-ethyl-imidazol-2-yl (C₂H₅—N) | |
| CH₃ | CH₃ | H | 1,5-dimethyl-imidazol-2-yl (CH₃—N, CH₃) | |
| CH₃ | CH₃ | H | 1-ethyl-pyrrol-2-yl (C₂H₅—N) | |
| CH₃ | CH₃ | H | 3-methylthio-thiophen-2-yl (CH₃S, S) | |
| CH₃ | CH₃ | H | 3-methyl-isoxazol-5-yl (N—O, CH₃) | |
| CH₃ | CH₃ | H | 3-methyl-thiazol-2-yl (N, S, CH₃) | |

TABLE 7-continued

| R | R¹ | R² | J | m.p.(°C) |
|---|----|----|---|----------|
| CH₃ | CH₃ | H | methyl-dihydro-isoxazole (CH₃, O, N—O) | |
| CH₃ | CH₃ | H | methyl-furo-isoxazole (CH₃, O, N—O) | |
| CH₃ | CH₃ | H | dimethyl-imidazo[1,2-a]pyrimidinyl (CH₃, CH₃) | |
| CH₃ | CH₃ | H | dimethyl-triazolo-pyrimidinyl (CH₃, CH₃) | |

Compounds of Formula I have been found to adversely affect the growth of some plants, many of which are commonly considered as weeds, and therefore to be useful for controlling the growth of such unwanted plants. Compounds of Formula I have been found to have selectivity with respect to some crop plants such as corn, soybeans and cotton—i.e., they control weeds at dosages at which they do not significantly harm the crop plants—particularly when applied pre-emergence or preplant incorporated (applied to and/or mixed with the soil before the seeds have sprouted.)

Accordingly, the invention includes a method of combatting unwanted plants which comprides applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants.

For application, a compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides—i.e., horticulturally acceptable carriers—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or penta-erythritol; condensates of these with ethylene oxide and/or propylene oxide; condensation products of fatty alcohols or alkyl phenols, for example, p-octylphenol or p-octylcresiol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound.

Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:

|  | Abbreviation |
|---|---|
| Barnyardgrass (watergrass) - *Echinochloa crus-galli* | BYGR |
| Downy brome - *Bromus tectorum* | DOBR |
| Yellow foxtail - *Setaria glauca* | YEFT |
| Sicklepod - *Cassia obtusifolia* | SIPO |
| Velvetleaf - *Abutilon theophrasti* | VELE |
| Garden cress - *Lepidium sativum* | GACR |
| Johnsongrass - *Sorghum halepense* | JOGR |
| Morningglory - *Ipomoea spp* | MOGL |
| Field bindweed - *Convolvulus arvensis* | FIBW |
| Nightshade - *Solanum sp.* | NISH |
| Blackgrass - *Alopecurus myosuroides* | BLGR |
| Yellow millet - *Panicum miliceum* | YEMI |
| Large crabgrass - *Digitaria sanguinalis* | LACG |
| Redroot pigweed - *Amaranthus retroflexus* | RRPW |
| Hemp sesbania - *Sesbania exaltata* | HESE |
| Prickly sida - *Sida spinosa* | PRSI |

TEST PROCEDURES

The preemergence (soil) herbicidal activity of compounds of Formula I was evaluated by planting seeds of downy brome, johnsongrass, yellow foxtail, barnyardgrass, yellow millet, blackgrass, hemp sesbania, velvetleaf, morningglory, prickly sida, sicklepod and garden cress in test tubes, nominally measuring 25×200 millimeters, filled about three-quarters full of untreated soil, in each case covered on top with about 2.5 cubic centimeters of soil, treated with 0.1 milligram of the test compound, to give a dosage of 1.0 pound of test compound per acre. The seeds were planted on top of the treated soil and covered with about 1.5 cubic centimeters of untreated soil. The planted soil was held under a controlled regimen of temperature, moisture, and light. At 10 days, the amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula I was evaluated by spraying 9-day-old large crabgrass plants, 9-day-old pigweed plants, 6-day-old johnsongrass plants, 9-day-old velvetleaf plants, 8-day-old yellow foxtail plants, 9-dayold sicklepod plants, 5-day-old morningglory plants, 5-day-old barnyardgrass plants, 6-day-old yellow millet plants, 9-day-old nightshade plants, 9-day-old prickly sida plants and 7-day-old field bindweed plants to runoff with 2.4 milliliters of a liquid formulation containing 0.5 milligram of the test compound (one pound of the test compound per acre). The sprayed plants were held under a controlled regimen of temperature, moisture and light for 7 to 8 days, when the effect of the test compound was evaluated visually, the results being rated on the 0 to 9 scale described above.

Results of the postemergence herbicidal activity tests are set forth in Tables I and II.

TABLE I

| Cmpd. No. | Preemergence Herbicidal Activity | | | | | | | | | | | |
|---|---|---|---|---|---|---|---|---|---|---|---|---|
|  | DOBR | JOGR | YEFT | BYGR | YEMI | BLGR | HESE | VELE | MOGL | PRSI | SIPO | GACR |
| 1 | 2 | —(a) | 2 | — | — | — | — | 4 | 8 | — | — | — |
| 2 | 4 | 6 | 6 | 8 | 6 | 0 | 8 | 5 | 8 | 7 | 7 | 4 |
| 3 | 2 | 3 | 3 | 4 | 1 | 0 | 2 | 3 | 7 | 2 | 2 | 2 |
| 4 | 8 | 8 | 7 | 8 | 8 | 7 | 9 | 9 | 9 | 8 | 7 | 8 |
| 5 | 0 | 5 | 3 | 3 | 0 | 6 | 0 | 0 | 6 | 0 | 4 | 6 |
| 6 | 0 | —(a) | 0 | — | — | — | — | 0 | 0 | — | — | — |
| 7 | 5 | 3 | 5 | 8 | 8 | 3 | 5 | 8 | 9 | 8 | 8 | 8 |
| 8 | 8 | — | 6 | — | — | — | — | 8 | 9 | — | — | — |
| 9 | 0 | 2 | 0 | 0 | 0 | 0 | 2 | 2 | 7 | 0 | 0 | 5 |
| 10 | 9 | 7 | 8 | 9 | 8 | 5 | 9 | 8 | 9 | 9 | 9 | 8 |
| 11 | 2 | 2 | 2 | 2 | 0 | 0 | 4 | 4 | 4 | — | 2 | 7 |
| 12 | 0 | 0 | 2 | 3 | 0 | 2 | 5 | 3 | 5 | 3 | 3 | 5 |
| 13 | 7 | 3 | 0 | 7 | 0 | 3 | 9 | 7 | 9 | 3 | 8 | 9 |
| 14 | 6 | 7 | 8 | 9 | 8 | 7 | 9 | 9 | 9 | 8 | 9 | 9 |
| 15 | 0 | 0 | 0 | 2 | 0 | 3 | 2 | 3 | 3 | 2 | 0 | 6 |
| 16 | 3 | 2 | 3 | 6 | 0 | 0 | 8 | 8 | 8 | 3 | 9 | 8 |
| 17 | 0 | 3 | 0 | 8 | 0 | 4 | 7 | 5 | 8 | 3 | 3 | 9 |
| 18 | 0 | 0 | 0 | 0 | 0 | 0 | 0 | 0 | 4 | 0 | 0 | 4 |
| 19 | 7 | 6 | 7 | 8 | 8 | 4 | 9 | 8 | 9 | 8 | 9 | 8 |
| 20 | 9 | 3 | 4 | 9 | 7 | 5 | 9 | 8 | 7 | 9 | 7 | 8 |
| 21 | 5 | 4 | 2 | 6 | 5 | 4 | 8 | 6 | 8 | 3 | 4 | 7 |
| 22 | 2 | 2 | 2 | 0 | 2 | 3 | 8 | 7 | 8 | 0 | 6 | 7 |
| 23 | 0 | 0 | 0 | 0 | 0 | 0 | 0 | 5 | 5 | 0 | 0 | 0 |
| 24 | 2 | 0 | 0 | 0 | 0 | 0 | 0 | 0 | 0 | 0 | 3 | 0 |
| 25 | 0 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 | 0 |
| 27 | 4 | 6 | 6 | 8 | 7 | 4 | 8 | 8 | 9 | 8 | 7 | 9 |
| 28 | 4 | 6 | 4 | 9 | 7 | 0 | 8 | 9 | 8 | 8 | 8 | 8 |
| 29 | 2 | 5 | 3 | 4 | 2 | 0 | 8 | 3 | 8 | 3 | 2 | 8 |

TABLE I-continued

Preemergence Herbicidal Activity

| Cmpd. No. | DOBR | JOGR | YEFT | BYGR | YEMI | BLGR | HESE | VELE | MOGL | PRSI | SIPO | GACR |
|---|---|---|---|---|---|---|---|---|---|---|---|---|
| 30 | 7 | 7 | 3 | 9 | 7 | 0 | 8 | 8 | 8 | 3 | 3 | —(a) |
| 31 | 6 | 6 | 8 | 9 | 8 | 4 | 7 | 8 | 8 | 8 | 9 | 8 |
| 32 | 0 | 0 | 0 | 0 | 0 | 0 | 0 | 0 | 0 | 0 | 0 | 0 |
| 33 | 0 | 5 | 5 | 8 | 7 | 3 | 8 | 6 | 9 | 0 | 6 | 8 |
| 34 | 8 | 8 | 7 | 9 | 7 | 3 | 7 | 7 | 7 | 9 | 7 | 7 |
| 35 | 0 | 7 | 0 | 0 | 0 | 0 | 8 | 5 | 3 | 3 | 2 | 4 |
| 36 | 2 | 5 | 3 | 4 | 2 | 2 | 3 | 5 | 4 | 2 | 4 | 8 |
| 37 | 0 | 0 | 0 | 0 | 0 | 0 | 0 | 0 | 0 | 0 | 0 | 0 |
| 38 | 0 | 0 | 0 | 0 | 0 | 0 | 0 | 0 | 0 | 0 | 0 | 0 |
| 39 | 6 | 5 | 3 | 3 | 2 | 3 | 9 | 4 | 9 | 3 | 8 | 4 |

(a) indicates that the compound was not tested with respect to this species.

TABLE II

Postemergence Herbicidal Activity

| Cmpd. No. | LACG | JOGR | YEFT | BYGR | YEMI | RRPW | NISH | VELE | MOGL | PRSI | SIPO | FIBW |
|---|---|---|---|---|---|---|---|---|---|---|---|---|
| 1 | —(a) | 2 | 8 | — | — | — | — | 3 | 4 | — | — | — |
| 2 | 3 | 3 | 3 | 3 | 5 | 3 | 4 | 3 | 7 | 3 | 5 | 4 |
| 3 | 4 | 5 | 5 | 6 | 9 | 4 | 7 | 5 | 9 | 5 | 9 | 9 |
| 4 | 0 | 5 | 9 | 7 | 5 | 6 | 3 | 2 | 7 | 3 | 7 | 5 |
| 5 | 0 | 4 | 3 | 4 | 4 | 3 | 7 | 3 | 8 | 3 | 5 | 5 |
| 6 | —(a) | 5 | 5 | — | — | — | — | 4 | 7 | — | — | — |
| 7 | 3 | 3 | 3 | 9 | 6 | 8 | 9 | 7 | 9 | 7 | 9 | 7 |
| 8 | — | 5 | 4 | — | — | — | — | 9 | 7 | — | — | — |
| 9 | 0 | 5 | 3 | 3 | 7 | 4 | 6 | 0 | 6 | 4 | 5 | 3 |
| 10 | 3 | 5 | 9 | 3 | 4 | 5 | 7 | 9 | 8 | 5 | 9 | 9 |
| 11 | 3 | 4 | 9 | 6 | 6 | 8 | 9 | 9 | 9 | 5 | 9 | 9 |
| 12 | 7 | 6 | 9 | 7 | 5 | 5 | 9 | 6 | 9 | 7 | 9 | 9 |
| 13 | 2 | 2 | 2 | 2 | 5 | 5 | 8 | 5 | 8 | 3 | 7 | 5 |
| 14 | 0 | 0 | 7 | 0 | 3 | 3 | 5 | 7 | 6 | 6 | 7 | 5 |
| 15 | 6 | 7 | 7 | 5 | 5 | 8 | 9 | 7 | 9 | 5 | 9 | 9 |
| 16 | 3 | 6 | 6 | 3 | 4 | 7 | 6 | 6 | 7 | 3 | 9 | 9 |
| 17 | 7 | 9 | 9 | 9 | 8 | 9 | 9 | 9 | 9 | 7 | 9 | 9 |
| 18 | 3 | 9 | 9 | 6 | 8 | 7 | 8 | 4 | 7 | 5 | 7 | 8 |
| 19 | 7 | 4 | 9 | 2 | 7 | 7 | 9 | 9 | 8 | 4 | 8 | 8 |
| 20 | 7 | 6 | 7 | 6 | 7 | 8 | 9 | 6 | 9 | 5 | 9 | 9 |
| 21 | 0 | 4 | 7 | 9 | 4 | 3 | 0 | 0 | 8 | 0 | 5 | 5 |
| 22 | 0 | 5 | 3 | 0 | 2 | 0 | 0 | 3 | 7 | 0 | 4 | 5 |
| 23 | 7 | 7 | 6 | 8 | 5 | 6 | 8 | 5 | 8 | 4 | 8 | 9 |
| 24 | 4 | 5 | 4 | 4 | 0 | 7 | 0 | 7 | 9 | 0 | 8 | 0 |
| 25 | 4 | 3 | 9 | 4 | 3 | 4 | 9 | 4 | 9 | 4 | 5 | 9 |
| 26 | 4 | 6 | 7 | 3 | 7 | 5 | 9 | 5 | 9 | 3 | 9 | 9 |
| 27 | 0 | 5 | 3 | 5 | 7 | 5 | 7 | 3 | 8 | 3 | 7 | 5 |
| 28 | 3 | 5 | 9 | 3 | 6 | 7 | 8 | 7 | 8 | 7 | 9 | 8 |
| 29 | 0 | 4 | 0 | 0 | 5 | 6 | 7 | 3 | 7 | 3 | 6 | 5 |
| 30 | 3 | 5 | 0 | 7 | 7 | 7 | 7 | 6 | 7 | 4 | 9 | 7 |
| 31 | 2 | 3 | 4 | 2 | 3 | 4 | 8 | 7 | 7 | 5 | 8 | 5 |
| 32 | 6 | 0 | 0 | 3 | 4 | 0 | 4 | 2 | 6 | 4 | 4 | 4 |
| 33 | 3 | 6 | 9 | 5 | 9 | 9 | 6 | 7 | 8 | 3 | 9 | 6 |
| 34 | 5 | 3 | 6 | 5 | 9 | 5 | 8 | 5 | 7 | 7 | 9 | 7 |
| 35 | 4 | 2 | 7 | 4 | 8 | 6 | 9 | 5 | 8 | 4 | 8 | 7 |
| 36 | 3 | 0 | 7 | 3 | 3 | 3 | 4 | 3 | 8 | 5 | 5 | 5 |
| 37 | 3 | 4 | 6 | 0 | 3 | 8 | 5 | 3 | 9 | 3 | 7 | 4 |
| 38 | —(a) | 3 | 3 | 0 | 0 | 3 | 3 | 4 | 7 | 0 | 5 | 3 |
| 39 | 3 | 4 | 3 | 2 | 5 | 5 | 7 | 5 | 7 | 2 | 4 | 7 |

(a) indicates that the compound was not tested with respect to this species.

We claim:

1. A compound of the formula

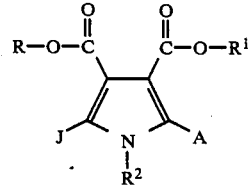

(I)

wherein

R and R¹ each independently is alkyl, mono- or polyhaloalkyl, alkenyl or alkynyl of up to four carbon atoms, and A is $C_1$ to $C_3$ alkyl;

J is

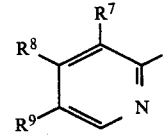

J-5 wherein

R² is (a) hydrogen;
(b) hydroxymethyl;
(c) —B(alkyl)₂ of two to six carbon atoms;
(d) —C(O)R¹⁷ wherein R¹⁷ is $C_1$-$C_4$ alkyl, $C_5$ to $C_6$ cycloalkyl, phenyl or pyridinyl substituted by one or more halogen atoms and/or by one of alkoxy, alkylthio, alkyl, alkoxycarbonyl, carbonyl, alkylsulfinyl or alkylsulfonyl; such that the total number of carbon atoms is one to eight;
(e) —CH₂—O—C(O)—R¹⁸ wherein R¹⁸ is $C_1$-$C_4$ alkyl, $C_5$ to $C_6$ cycloalkyl, phenyl or pyridinyl substituted by one or more halogen atoms and/or one of alkoxy, alkylthio, alkyl, alkoxycarbonyl, carboxyl, alkylsylfinyl or alkylsulfonyl; such that the total number of carbon atoms is one to eight;
(f) —S—C(O)O—R¹⁹, wherein R¹⁹ is $C_4$ alkyl or phenyl;

R⁷, R⁸ and R⁹ each independently is hydrogen, halogen, trifluoroethoxy, difluoromethoxy, cyano, nitro, hydroxy, amino, alkyl, alkoxy, amono- or dialkoxyalkyl, alkylthio, mono- or dialkylamino, wherein each alkyl amino moiety is of one to four carbon atoms.

2. Compounds of claim 1 where

A is CH₃;

R is $C_1$ to $C_3$ alkyl, $C_2$ to $C_3$ haloalkyl, $C_3$ alkenyl or $C_3$ alkynyl;

R¹ is $C_1$ to $C_2$ alkyl;

R² is hydrogen, hydroxymethyl, C(O)R¹⁷ or CH₂OC(O)R¹⁸; and

R¹⁷ and R¹⁸ are independently $C_1$ to $C_4$ alkyl, $C_5$ to $C_6$ cycloalkyl, phenyl, or pyridinyl or such substituted by one or more of halogen atoms and/or one of alkoxy, alkylthio, alkyl, alkoxycarbonyl, carboxyl, alkylsulfinyl or alkylsulfonyl.

3. Compounds of claim 2 where

R⁷, R⁸ and R⁹ each independently is hydrogen, chlorine, or is $C_1$ to $C_4$ alkyl, alkoxy or alkylthio.

4. A compound of claim 3 where J is J-5.

5. A compound according to claim 1 wherein J is J-5 wherein R and R¹ each is alkyl, R⁷, R⁸ and R⁹ each is hydrogen, halogen, alkyl, alkoxy, alkylthio, difluoromethoxy, or mono- or dialkoxymethyl, and R² is hydrogen.

6. A composition suitable for controlling the growth of undesired vegetation which comprises an effective amount of a compound of claim 1 and at least one of the following: surfactant, solid or liquid diluent.

7. A composition suitable for controlling the growth of undesired vegetation which comprises an effective amount of a compound of claim 2 and at least one of the following: surfactant, solid or liquid diluent.

8. A composition suitable for controlling the growth of undesired vegetation which comprises an effective amount of a compound of claim 3 and at least one of the following: surfactant, solid or liquid diluent.

9. A composition suitable for controlling the growth of undesired vegetation which comprises an effective amount of a compound of claim 4 and at least one of the following: surfactant, solid or liquid diluent.

10. A method for controlling the growth of undesired vegetation which comprises applying to the locus to be protected an effective amount of a compound of claim 1.

11. A method for controlling the growth of undesired vegetation which comprises applying to the locus to be protected an effective amount of a compound of claim 2.

12. A method for controlling the growth of undesired vegetation which comprises applying to the locus to be protected an effective amount of a compound of claim 3.

13. A method for controlling the growth of undesired vegetation which comprises applying to the locus to be protected an effective amount of a compound of claim 4.

* * * * *